(12) United States Patent
Fleury et al.

(10) Patent No.: US 7,397,240 B2
(45) Date of Patent: Jul. 8, 2008

(54) METHOD OF MEASURING ROCK WETTABILITY BY MEANS OF NUCLEAR MAGNETIC RESONANCE

(75) Inventors: Marc Fleury, La Celle Saint Cloud (FR); Françoise Deflandre, Ermont (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 10/527,088

(22) PCT Filed: Aug. 18, 2003

(86) PCT No.: PCT/FR03/02544

§ 371 (c)(1),
(2), (4) Date: Oct. 3, 2005

(87) PCT Pub. No.: WO2004/025317

PCT Pub. Date: Mar. 25, 2004

(65) Prior Publication Data

US 2006/0132131 A1    Jun. 22, 2006

(30) Foreign Application Priority Data

Sep. 11, 2002  (FR) ................................. 02 11283

(51) Int. Cl.
*G01V 3/00* (2006.01)
*G01V 1/40* (2006.01)

(52) U.S. Cl. ............................. 324/303; 702/11; 702/12
(58) Field of Classification Search ................. 324/303; 702/6–18
See application file for complete search history.

(56) References Cited

U.S. PATENT DOCUMENTS

| 4,543,821 A | 10/1985 | Davis, Jr. |
| 5,162,733 A * | 11/1992 | Baldwin .................... 324/307 |
| 6,765,380 B2 * | 7/2004 | Freedman et al. .......... 324/303 |
| 2002/0067164 A1 | 6/2002 | Venkataramanan et al. |

FOREIGN PATENT DOCUMENTS

| EP | 0 974 839 A1 | 1/2000 |
| WO | WO 01/42817 A1 | 6/2001 |

* cited by examiner

*Primary Examiner*—Diego Gutierrez
*Assistant Examiner*—Dixomara Vargas
(74) *Attorney, Agent, or Firm*—Antonelli, Terry, Stout & Kraus, LLP.

(57) ABSTRACT

A method for measuring the wettability of rocks by low-field nuclear magnetic resonance is described which has application for hydrocarbon reservoir engineering or development, or in civil engineering. The method essentially determines the water wet pore surface and the oil wet pore surface when the sample is saturated with water and oil, by measurements of relaxation times (T1, T2) of the sample placed in a nuclear magnetic resonance device, previously brought to various water or oil saturation states, and calculating the wettability index by combination of values the relaxation times obtained for said surfaces.

14 Claims, 4 Drawing Sheets

METHOD OF MEASURING ROCK WETTABILITY BY MEANS OF NUCLEAR MAGNETIC RESONANCE

BACKGROUND OF THE INVENTION

1. Field of the Invention

The present invention relates to a method for measuring the wettability of rock samples by measuring the relaxation time by low-field nuclear magnetic resonance.

2. Description of the Prior Art

There are well-known methods for determining the wettability of rocks to contained water and oil, comprising carrying out rock drainage cycles, that is displacement of fluids intended to decrease the water saturation, followed by imbibition. Imbibition relates to a displacement of fluids allowing an increase in the water saturation (Sw) of the rock. The capillary pressure Pc at one point is defined as the difference at equilibrium between the pressure P(oil) of the oil and the pressure P(water) of the water. This parameter is useful only if the two fluids are in the continuous phase in the porous medium. For a water wet medium, only the positive values are useful. On the other hand, when the medium has a mixed wettability, the fluids can remain in the continuous phase for the positive as well as for the negative capillary pressures (Pc).

For an application of this type, a complete capillary pressure measuring cycle generally comprises (FIG. 1):

a) positive primary drainage of an initially 100% water-saturated sample (curve 1);

b) positive imbibition (curve 2);

c) negative imbibition (curve 3);

d) negative drainage (curve 4); and e) positive secondary drainage (curve 5); and wherein f) Swir is the irreducible water saturation discussed below in the Practical implementation example, Sor is the residual oil saturation also discussed below in the Practical implementation example, and Ad and Ai are surface areas discussed below and are used in the definition of the wettability indices WI.

The curves represent evolution of Pc as a function of Sw with Swir being a specific value of SW.

There are various types of devices allowing the curves of FIG. 1 to be drawn.

In a device referred to as a "porous plate" device, notably described in U.S. Pat. No. 4,506,542, the porous rock sample containing two fluids in the continuous phase is placed in an elongate cell ended at its two opposite ends by capillary barriers permeable to a first fluid. This first fluid is injected under pressure through the first membrane and the pressure difference between the injection pressure and the pressure of the fluid discharged at the other end is measured. The pressures of the two fluids and the capillary pressure Pc are constant all along the sample, and the saturation is assumed to be uniform.

It is also known to carry out progressive-speed centrifugation by means of centrifugation devices such as those described for example in French Patent 2,772,477 corresponding to U.S. Pat. No. 6,185,985 or French Patent 2,763,690, or European Patent 603,040 corresponding to U.S. Pat. No. 5,463,894 or French Patent 2,798,734 filed by the Assignee.

The sample initially saturated with a first liquid (brine for example) is placed (FIG. 8) in an elongate vessel or cup A containing a second fluid of different density (oil for example). Cup A is fastened to the end of a rotating arm B and a centrifugal force is applied thereto so as to study the displacements of the fluids in the sample during at least two distinct steps. During a first drainage step, the assembly is then subjected to a centrifugal force applied along the length of the vessel so as to exert an expulsion force which tends to cause part of the first fluid to flow out. The pressure field created by centrifugation is expressed as a function of the density $\rho$, of the radius R and of the angular velocity w, by the relation: $½w^2**·\pi(Rmax^2-R^2)$, for each fluid. The pressure of the two fluids at the sample outlet is the same and is equal to zero at the outlet. At the same time, the second fluid flows into the sample. The two fluids move in the sample until a position of equilibrium is reached where the force due to the capillary pressure in the pores compensates for the centrifugal force exerted. A measuring sonde is placed in the cup on the side of the sample. The sonde can be of capacitive type for example and comprise a metal rod insulated by a ceramic sheath. The capacity between the rod and the conducting fluid (brine), which is proportional to the immersed height, is measured. With this measuring system, the measuring accuracy is 1.5% of the pore volume. The sonde detects the position of the interface between the two liquids in the cup and transmits the measuring signals to a measuring signal acquisition and control automaton E including hydraulic liquid circulation means and an acquisition device.

During the re-imbibition stage, the velocity is decreased so as to study the return of the initial fluid into the sample. The local saturations measured with this type of device are calculated by an inversion program from the total amount of water expelled from the sample.

According to another method, referred to as a "dynamic" method, a sample is placed in an elongate cell having water-permeable membranes at its two ends. At a first end, oil under pressure is directly injected into the enclosure. Water is also injected, but this injection is carried out through the membrane and at a lower pressure. At the opposite end, the oil is directly discharged whereas the water flows out through the terminal membrane. Adjustment of the oil and water injection rates allows the capillary pressure to be the same at the inlet and at the outlet of the enclosure, which leads to a uniform saturation that can be deduced from the fluids balance. The capillary pressure is obtained for example by measuring the difference between the pressure of the oil and of the water at the enclosure outlet. Such a method is notably described by Brown H. W. in "Capillary Pressure Investigations", Petroleum Transaction AIME, vol. 192, 1951. Examples of implementation are for example described in patents European Patent 729,022 corresponding to U.S. Pat. No. 5,698,772 or EP Patent 974,839 corresponding to U.S. Pat. No. 6,229,312 field by the Assignee.

A method referred to as semi-dynamic method is also known, wherein a rock sample imbibed with a first fluid is confined in a closed cell, another fluid under pressure is injected at a first end of the enclosure and the opposite end is swept by a low-pressure fluid circulated by a pump which carries the drained fluid outside. The device measures the pressure and the saturation of the sample, the amount of fluid discharged and the electric resistivity of the sample. This method is implemented for example in French Patent 2,708,742 corresponding to U.S. Pat. No. 5,679,885 filed by the Assignee.

Once drainage and imbibition curves are established, it is well-known to calculate the wettability indices WI from the surface areas Ad and Ai marked by the positive and negative capillary pressure curves, as shown in FIG. 1, by the relation $$WI_{(USBM)} = \text{Log} \frac{A_d}{A_i}.$$

SUMMARY OF THE INVENTION

The method for measuring the wettability of a porous rock sample in the presence of water and oil according to the invention comprises determining the water wet pore surface and the oil wet pore surface when the sample is saturated with water and oil, and calculating the wettability index by combination of the values obtained for said surfaces.

The method finds applications notably for analysis of rocks taken from an underground formation containing or likely to contain hydrocarbons.

Knowledge of various parameters, and notably of the wettability of the rocks, is also useful notably for enhanced recovery of a formation, by injection of a fluid under pressure, and when the fluid (liquid or gas) best suited for effluents displacement is to be determined by means of preliminary tests.

The invention also finds applications in civil engineering for formation hydrology in order to evaluate the degree of pollution of formations for example, or in the building trade for testing building materials notably in order to determine waterproofing treatments for example.

Determination of the water wet pore surface and of the oil wet pore surface when the sample is saturated with water and oil is obtained for example by means of measurements of relaxation times of the sample placed in a nuclear magnetic resonance device.

The wettability index is for example determined by the relation $$I_{NMR} = \frac{SM_w - SM_o}{SM_w + SM_o} \text{ or the relation } I_{NMR} = \log_{10} \frac{SM_w}{SM_o}$$

where $SM_w$ is the water wet pore surface and $SM_o$ is the oil wet pore surface when the porous medium is saturated with water and oil.

According to an implementation mode, the wettability index is determined by the following operations:

a) measuring the characteristic relaxation times of the water-saturated sample;

b) measuring the characteristic relaxation times of the oil in the sample in the presence of water, in a zone close to saturation (Swir) of the sample;

c) measuring the characteristic relaxation times of the water in the sample in the presence of oil, in a zone close to residual saturation (Sor);

d) measuring the relaxation times of the sample in a state where its 100% oil saturation point is reached; and e) combining the measurements of the various relaxation times so as to obtain the index.

According to a preferred implementation mode, the relaxation times of operations a) to c) are determined after subjecting the sample to centrifugation.

According to a preferred implementation mode, the relaxation times of operation d) are determined after forced displacement of the fluids in the sample placed in a containment cell.

An oil whose intrinsic relaxation time ($T_B$) is as great as possible and as close as possible to that of water, dodecane for example, is preferably selected.

The characteristic relaxation times are for example those corresponding to either the saturation curves maxima, or to mean values of the curves.

Experience shows that the measurement of $I_{NMR}$ obtained by means of the method is as sensitive but requires much less time and is applicable to a large number of samples.

BRIEF DESCRIPTION OF THE DRAWINGS

Other features and advantages of the method and of the device according to the invention will be clear from reading the description hereafter of an embodiment given by way of non limitative example, with reference to the accompanying drawings wherein.

DETAILED DESCRIPTION OF THE INVENTION

It should be noted that the NMR analysis technique essentially applies to an object to be tested a first static magnetic polarization field Bo intended for aligning the initially randomly oriented hydrogen protons nuclei in the direction of the field, then a second impulsive magnetic field oscillating at the Larmor frequency, perpendicular to the first one, created by coils excited by a control signal to carry out a nuclear magnetic resonance experiment. When this impulsive field stops, the return of the nuclei to their initial state or relaxation generates electromagnetic signals (echoes) which are detected and analyzed. The presence of physical parameters of the object is determined from the amplitude characteristics of these signals.

A new wettability index is constructed by combining values of the water wet pore surface $SM_w$ and of the oil wet pore surface $SM_o$ when the porous medium is saturated with water and oil. The index can be calculated for example by the relation as follows:

$$I_{NMR} = \frac{SM_w - SM_o}{SM_w + SM_o} \quad (1a)$$

or by the relation:

$$I_{NMR} = \log_{10} \frac{SM_w}{SM_o} \quad (1b)$$

Quantities $SM_w$ and $SM_o$ are obtained for example by measuring the dominant relaxation time in a low-field nuclear magnetic resonance experiment.

In fact, in such an experiment, the fundamental relation connecting the longitudinal $T_1$ or transverse $T_2$ relaxation time to surface S and to the volume of this pore is as follows:

$$\frac{1}{T_{1,2}} = \frac{1}{T_{1B,2B}} + \rho_{1,2}\frac{S}{V} \quad (2)$$

where $T_{1B,2B}$ is the relaxation time of the fluid outside the porous medium. Basically, this relation comes from the fact that the molecules in the pore undergo diffusion motions and interact with the porous wall during the measuring time (the typical relaxation time is of the order of 100 ms). The surface interactions are designated by coefficient $\pi_{1,2}$ referred to as surface relaxivity. A gradient term is discarded that is important when measurements are performed at a high magnetic field (>0.1 T). Relation 2 is strictly valid for a pore saturated with a single fluid. In general, natural porous media have a pore size and therefore ratio S/V distribution. A relaxation times distribution is thus generally observed, but this does not modify the method described here.

Figure 2A:
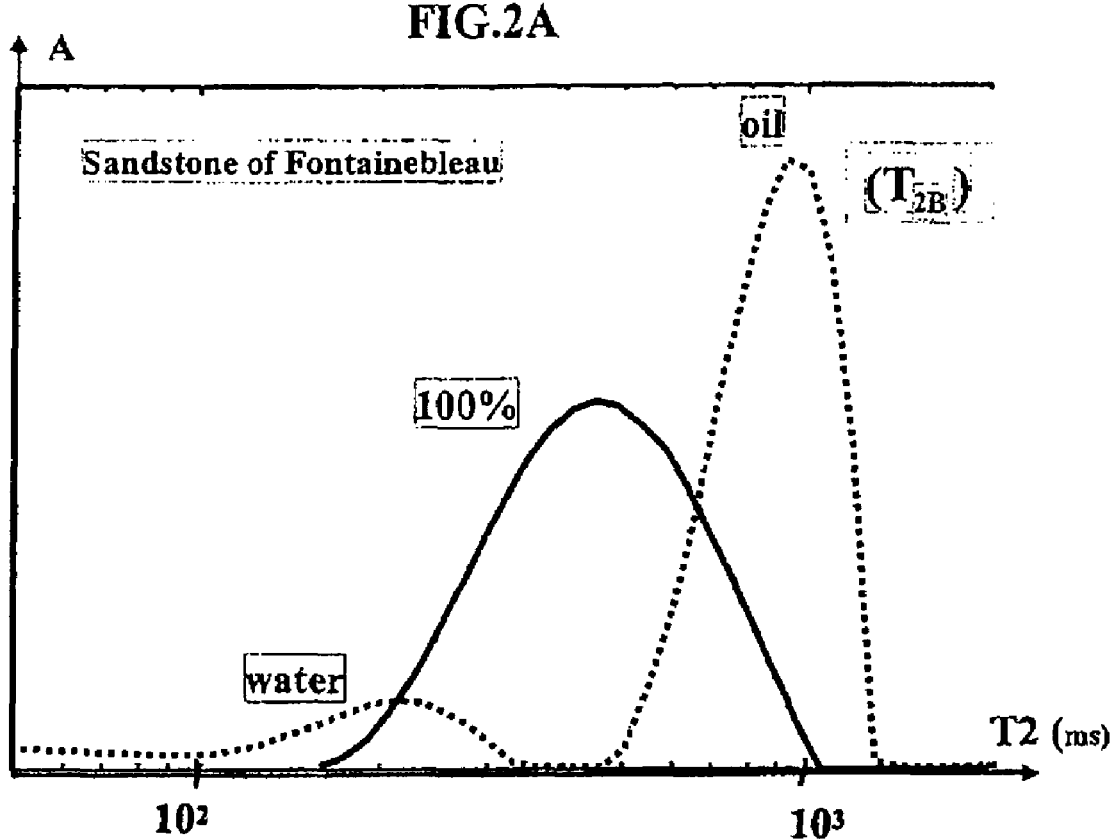
FIGS. 2A and 2B respectively show the distribution of relaxation times $T_2$ for a water wet rock saturated with water and oil, and a representation of the phase distribution (matrix in hatched lines, water in light grey and oil in darker grey)
Figure 2B:
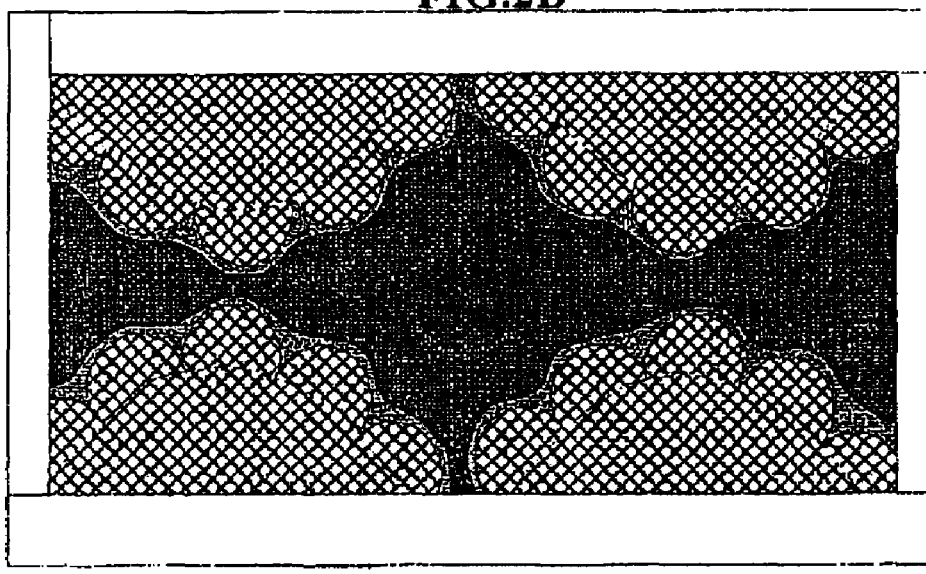
Figure 3A:
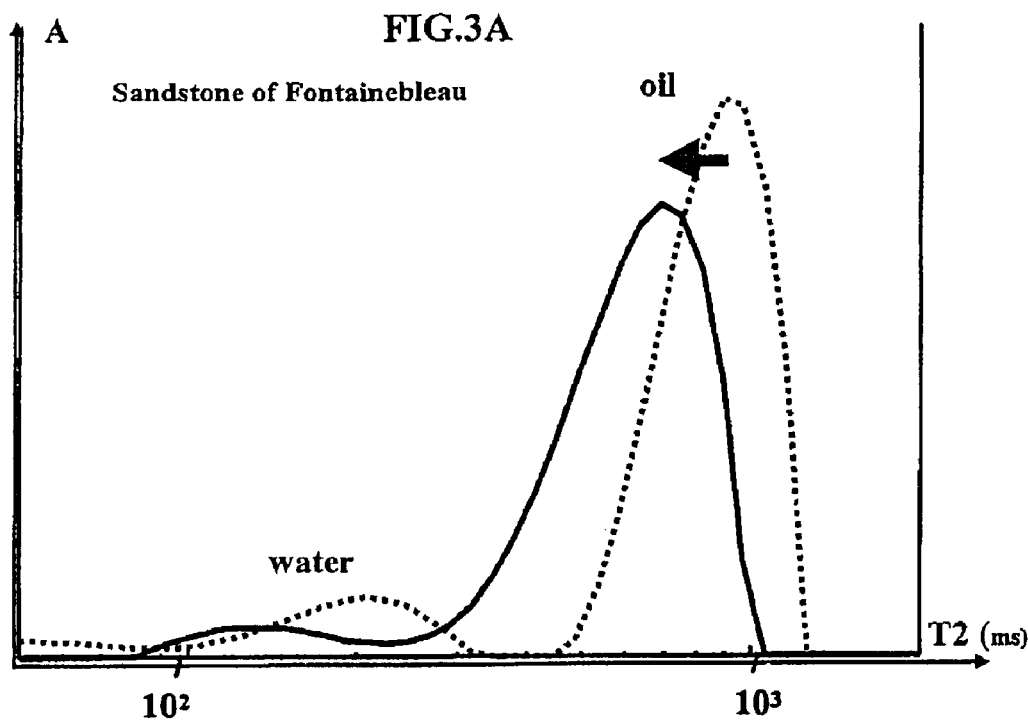
FIGS. 3A and 3B respectively show the distribution of relaxation times $T_2$ for a rock of intermediate wettability saturated with water and oil (same central part as in FIG. 2), and a representation of the phase distribution (matrix in hatched lines, water in light grey and oil in darker grey)
Figure 3B:
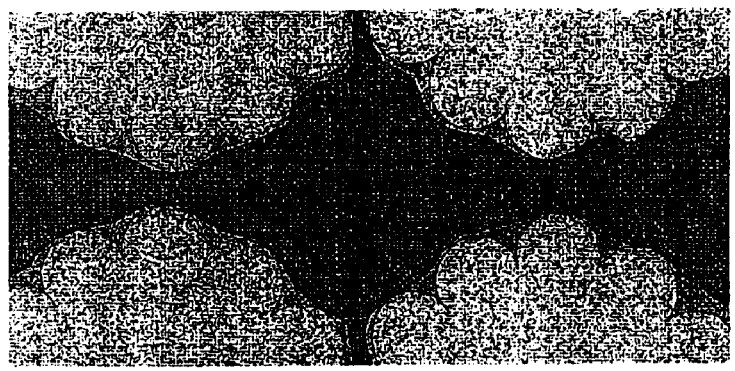

When two fluids are present in a pore within the porous medium, the same physical diffusion mechanism is valid, but the distribution of the two fluids in relation to the pore surface is of crucial importance. For example, when the medium is water wet, the water is at the surface and interacts therewith, whereas the oil is inside the pore and does not interact with the surface. When the distribution of the relaxation times is measured for such a system, the result of FIG. 2A is observed. The water has shorter relaxation times than in the case of a 100% water saturation, because the volume of water V has decreased (see equation 1). The oil is characterized by a relaxation time that is the same as when the measurement is performed outside the porous medium ($T_{1B,2B}$) because there is no interaction with the pore surface. Besides, it is well-known that interactions at the water/oil interface do not lead to a relaxation that is different from that of the oil outside the porous medium, provided that the oil considered is light (refined oil such as dodecane). Diagrammatically, the phase distribution is shown in FIG. 2B. When the same porous medium has a different wettability and is not clearly water wet, the distribution of the relaxation times is modified (FIG. 3A). Essentially, the characteristic time of the oil will be shorter as a result of an interaction of the oil at the pore surface because the water is no longer the closer to the surface. The possible distribution of the two fluids is shown in FIG. 3B. Such an effect has been obtained using standard procedures allowing to reproduce the surface properties of rocks from a petroleum reservoir: cleaning, then aging in the reservoir oil at the temperature of the reservoir at the irreducible water saturation.

The relation (2) is generalized to a two-phase water-oil system. For the water, the relationship is:

$$\frac{1}{T_{1w,2w}} = \frac{1}{T_{1Bw,2Bw}} + \rho_{1w,2w}\frac{SM_w}{V_w} \quad (3)$$

and for the oil:

$$\frac{1}{T_{1o,2o}} = \frac{1}{T_{1Bo,2Bo}} + \rho_{1o,2o}\frac{SM_o}{V_o}. \quad (4)$$

Thus quantities $SM_w$ and $SM_o$ can be determined by measuring relaxation times $T_1$ or $T_2$ in the porous medium, relaxation times $T_{1B}$ or $T_{2B}$ of the fluids outside the porous medium, liquid volumes $V_o$ or $V_w$ present in the porous medium. The interaction constants $\rho$ can be determined separately, but it will be seen that only the ratio of these constants is necessary.

Relations 3 and 4 are introduced in the base relation 1, which results in the relationship:

$$I_{NMR} = \frac{Sw\left(\frac{1}{T_w} - \frac{1}{T_{bw}}\right) - C\rho So\left(\frac{1}{T_o} - \frac{1}{T_{bo}}\right)}{Sw\left(\frac{1}{T_w} - \frac{1}{T_{bw}}\right) + C\rho So\left(\frac{1}{T_o} - \frac{1}{T_{bo}}\right)} \quad (5)$$

where $Sw=Vw/Vp$ is the water saturation, $So=Vo/Vp$ is the oil saturation, and $Vp$ the pore volume.

$$C\rho = \frac{\rho_w}{\rho_o}$$

is the ratio of the relaxivities for the water wet (w) and oil wet (o) surfaces. To simplify the notation, indices 1 and 2 have been suppressed.

Figure 1:
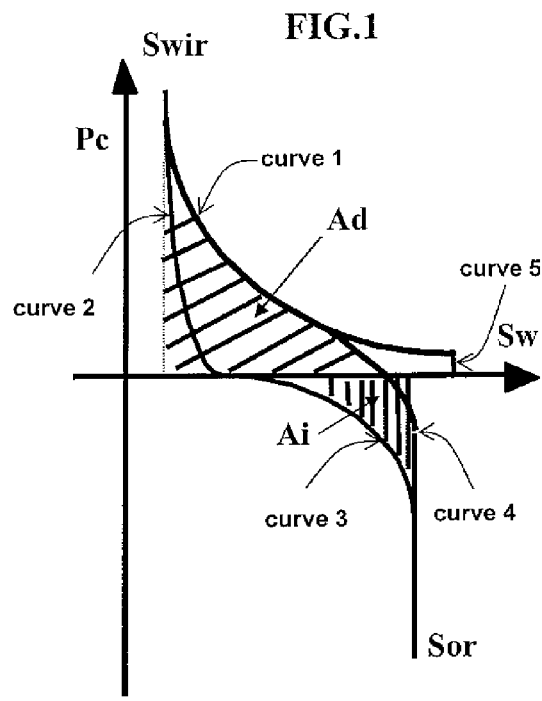
FIG. 1 shows examples of capillary pressure curves necessary for determination of the conventional wettability index $I_{USBM}$ (United States Bureau of Mines)
Figure 4:
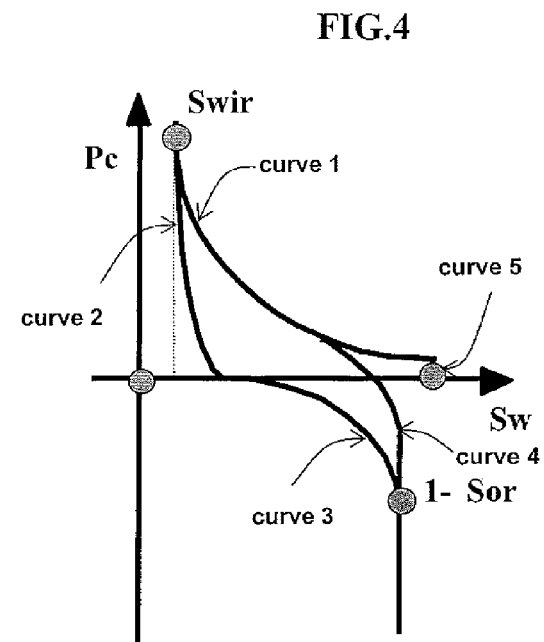
FIG. 4 shows, on capillary pressure curves, the saturation values where the NMR relaxation measurements are performed.

The most suitable saturations for measuring quantities $SM_w$ and $SM_o$ thus remain to be determined. For reasons linked with the calculation of the relaxation time distributions, the irreducible water saturation (Swir, FIG. 4, which is a specific value of SW) is selected to determine the oil wet surface in the presence of water ($SM_w$), and the residual oil saturation (Sor, FIG. 4) to determine the water wet surface in the presence of oil. Also, an oil whose intrinsic relaxation time ($T_B$) is as great as possible and as close as possible to water is selected. In fact, if $T_B$ is too small, the method will be limited to porous media whose ratio S/V is high (small pore sizes), or to media whose surface relaxivity is high. Dodecane for example is a refined oil which is suited to the proposed measurement because its intrinsic relaxation time ($T_{Bo}$) is 1 s, close to the relaxation time of water ($T_{Bw}$, about 2.7 s). Crude petroleum oils should generally not be used because their relaxation times are too small and they also have a relaxation time distribution which considerably hinders analysis. The practical details of the calculation are given below.

Figure 5:
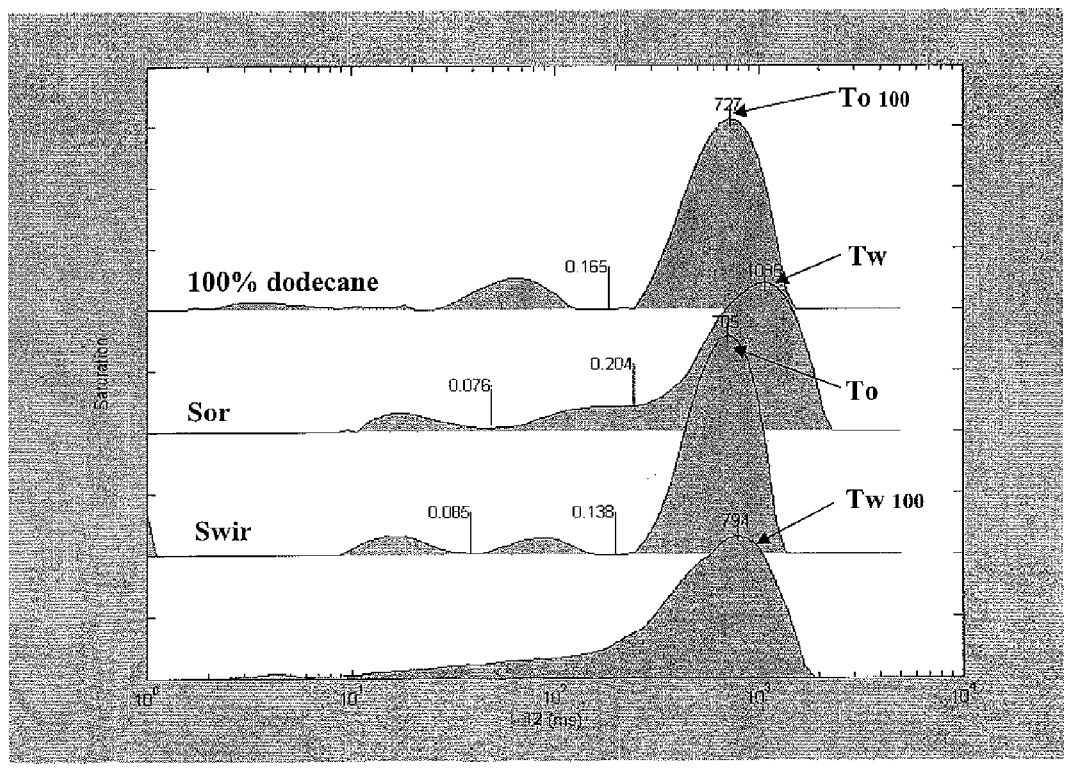
FIG. 5 shows an example of distribution of relaxation times $T_2$ at the saturation values given in FIG. 4 (from the bottom up: 100% water, Swi, Sor and 100% dodecane)

From the distribution of the relaxation times at the different saturations (See the example of FIG. 5), the relaxation time corresponding to the dominant peak (Tw at Sor, To at Swi) can be easily determined, and these values are used in relation 5. It is well-known that determination of the dominant relaxation time is robust and depends little on the distribution calculation process. It can be noted that the dominant peak corresponds to that of the oil at Swi and of the water at Sor. The presence of the second fluid at these different saturations is important from a physical point of view, but it disturbs calculation very little. It can be shown that whatever the relaxation time of the second fluid present in small amount (water at Swi, oil at Sor), the relaxation time of the dominant fluid does not fluctuate much. This aspect is important for the calculation robustness. FIG. 5 shows the distribution of the transverse relaxation times $T_2$. The longitudinal relaxation time $T_1$ can also be used, but this measurement is less favourable in general because $T_1 > T_2$ but $T_{1B} = T_{2B}$ for a given fluid.

In order to determine the surface relaxivity ratio $C\rho$, the dominant relaxation times $T_{w100}$ and $T_{o100}$ respectively at the two saturations Sw=100% are used and So=100%. The formula used is as follows:

$$C_\rho = \frac{\rho_w}{\rho_o} = \frac{1/T_{w100} - 1/T_{Bw}}{1/T_{o100} - 1/T_{Bo}}. \qquad (6)$$

FIG. 5 illustrates the two measurements performed. Thus, in total, the relaxation times distributions have to be measured at four saturations: 100% brine, 100% oil and the extreme saturations Swi and Sor. It is possible to therefore use the centrifugation technique to reach, starting from Sw=100%, Swi, then Sor. A single rotation stage at maximum speed allows these values to be rapidly reached. For measurement at So=100%, a succession of miscible displacements by injecting an alcohol, then the refined oil are used.

Implementation

For implementing the method, an NMR measuring device conventionally comprising (FIG. 7) magnets 1 with an air gap in which coils 2 are arranged is used. The coils are connected to an electronic box which generates the excitation signals (signals in the radio frequency range for example) creating an oscillating electric field for acquiring the response of sample S to the excitation signals. A device of this type is used for example in French patent 2,823,308.

Practical Implementation Example

Figure 7:
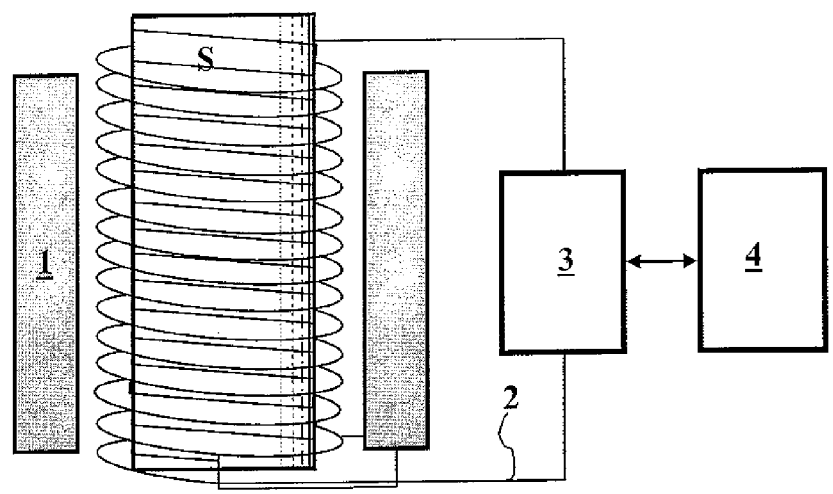
FIG. 7 diagrammatically shows a containment cell with a permanent heating circuit by fluid circulation.
Figure 8:
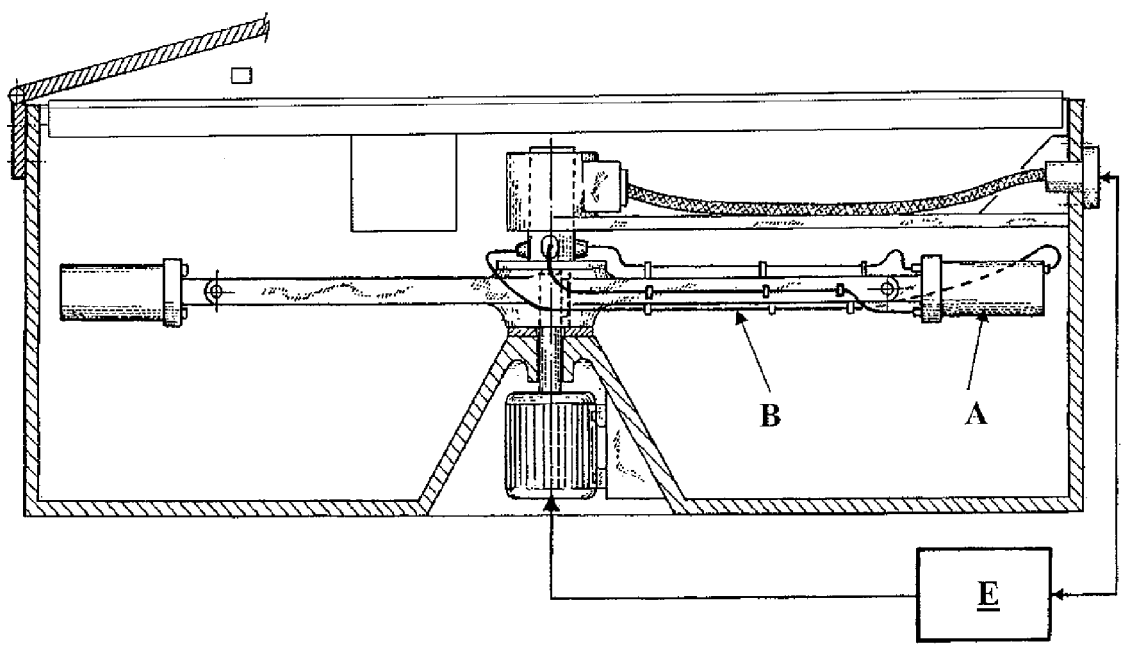
FIG. 8 diagrammatically shows the layout of a centrifugation device used for implementing the method.

The wettability index is obtained by carrying out for example the following succession of operation with a reservoir sample whose wettability is intermediate:

1. The sample is 100% saturated with reservoir brine and placed in the NMR measuring device (as shown in FIGS. 7-8 for example) to measure the distributions of relaxation times $T_1$, $T_2$ and to deduce parameter Tw100 of equation 6;

2. It is then placed in the centrifugation device (as schematized in FIG. 8) and centrifuged at maximum speed in a vessel filled with oil until the irreducible water saturation Swir is reached; the distributions of relaxation times $T_1$, $T_2$ are then measured in the NMR device so as to deduce $T_o$ of equation 5;

3. After being placed again in the centrifugation device, the sample is centrifuged at maximum speed until the residual oil saturation Sor is reached; it is then transferred into the NMR device again to measure relaxation times $T_1$, $T_2$ and to deduce $T_w$;

4. The sample is thereafter placed in a containment cell such as those described in the aforementioned patents and a water and oil miscible solvent, then oil (dodecane for example) is injected until the 100% oil saturation is reached. This point being reached, relaxation times $T_1$, $T_2$ are again measured in the NMR device and the value of $T_{o100}$ required for determination of $C_\rho$ is deduced.

Thus all the parameters for calculation of wettability coefficient $I_{NMR}$ are known.

Comparison with Index $I_{USBM}$

Figure 6:
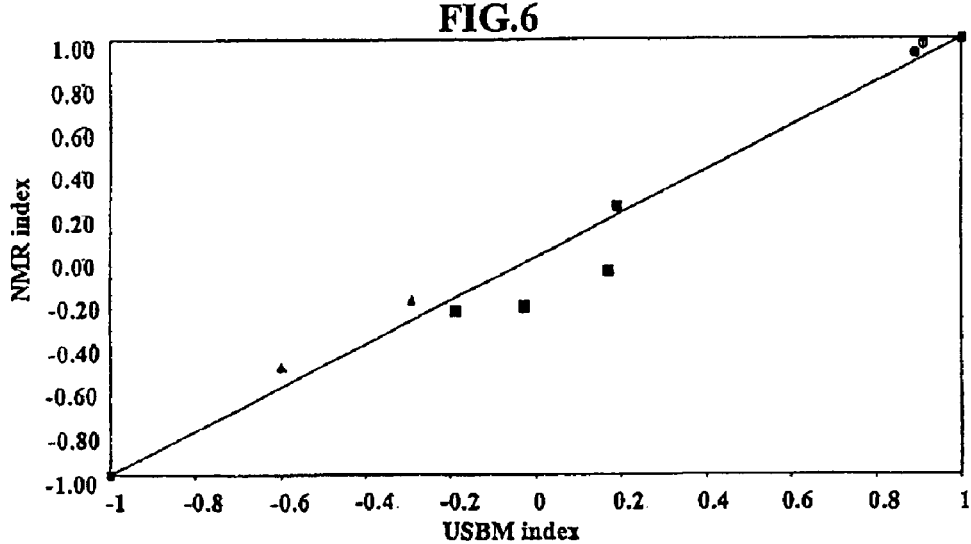
FIG. 6 shows the relation between index $I_{NMR}$ and the standard index $I_{USBM}$.

Comparison between wettability index $I_{USBM}$ and the new index $I_{NMR}$ shows a good correlation between these two quantities (FIG. 6) for reservoir rocks. The measurement of $I_{USBM}$ can therefore be advantageously replaced by a measurement of $I_{NMR}$, which is as sensitive but requires much less time and is applicable to a large number of samples.

An implementation is described example where a NMR type relaxometry method is used to measure the surface and the volume of the pores. This method is however not limitative. Any other analysis method can be used, notably cryomicroscopy.

The invention claimed is:

1. A method for analyzing a porous rock sample by measuring a wettability of the porous rock sample in a presence of water and oil, comprising determining a water wet pore surface of the sample and an oil wet pore surface of the sample when the sample is saturated with water and oil, and calculating a wettability index from a combination of the water wet pore surface and the oil wet pore surface wherein the water wet pore surface and of the oil wet pore surface is determined when the sample is saturated with water and oil from measurements of relaxation times obtained from the surfaces of the sample placed in a nuclear magnetic resonance device and calculating the wettability under index by:

a) measuring the relaxation times of the water-saturated sample;
   b) measuring the relaxation times of the sample in the presence of oil and water, in a zone approaching saturation of the sample;
   c) measuring the relaxation times of the oil in the sample in the presence of water, in a zone approaching saturation of the sample;
   d) measuring relaxation times of the sample in a state of 100% oil saturation;
   e) combining measurements of the relaxation times obtained from a)-d) so as to obtain the wettability index; and
   f) using the wettability index to analyze the porous rock sample.

2. A method as claimed in claim 1, wherein the wettability index is obtained by the relation:

$$I_{NMR} = \frac{SM_w - SM_o}{SM_w + SM_o}$$

where $SM_w$ is the water wet pore surface and $SM_o$ is the oil wet pore surface when the porous rock sample is saturated with water and oil.

3. A method as claimed in claim 2, wherein oil having an intrinsic relaxation time as great as possible and as close as possible to that of the water is selected.

4. A method as claimed in claim 1, wherein the wettability index is obtained by the relation:

$$I_{NMR} = \log_{10} \frac{SM_w}{SM_o}$$

where $SM_w$ is the water wet pore surface and $SM_o$ is the oil wet pore surface when the porous rock sample is saturated with water and oil.

5. A method as claimed in claim 4, wherein oil having an intrinsic relaxation time as great as possible and as close as possible to that of the water is selected.

6. A method as claimed in claim 1, wherein the relaxation times of a) to c) are measured after subjecting the sample to centrifugation.

7. A method as claimed in claim 6, wherein oil having an intrinsic relaxation time as great as possible and as close as possible to that of the water is selected.

8. A method as claimed in claim 1, wherein the relaxation times are measured after forced displacement of the fluids in the sample placed in a containment cell.

9. A method as claimed in claim 8, wherein oil having an intrinsic relaxation time as great as possible and as close as possible to that of the water is selected.

10. A method as claimed in claim 1, wherein oil having an intrinsic relaxation time as great as possible and as close as possible to that of the water is selected.

11. A method as claimed in claim 1, wherein the relaxation times are those corresponding to either a saturation curves maxima, or to mean values of the curves.

12. A method as claimed in claim 1, wherein the porous rock sample is obtained from an underground formation containing an effluent; and further comprising:
   determining a fluid suited for effluent displacement from the analyzing of the porous rock sample; and
   using the fluid suited for effluent displacement to provide enhanced recovery of the effluent from the formation by effluent displacement.

13. A method as claimed in claim 1, wherein the porous rock sample is obtained from an underground formation; and further comprising:
   evaluating a degree of pollution of the formation from the analyzing of the porous rock sample.

14. A method as claimed in claim 1 wherein the porous rock sample is a building material; and further comprising:
   using the analysis of the porous rock sample to determine a waterproofing treatment using the porous rock sample.

* * * * *